United States Patent
Przybylski et al.

(10) Patent No.: US 10,820,852 B2
(45) Date of Patent: Nov. 3, 2020

(54) ALLERGIC EARLY DETECTION WEARABLE DEVICE

(71) Applicant: International Business Machines Corporation, Armonk, NY (US)

(72) Inventors: Kevin J. Przybylski, Rochester, MN (US); Joseph Kuczynski, North Port, FL (US); Debra A. Neuman-Horn, Rochester, MN (US); Marvin M. Misgen, Rochester, MN (US); Joseph F. Prisco, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/223,515

(22) Filed: Dec. 18, 2018

(65) Prior Publication Data

US 2020/0187846 A1 Jun. 18, 2020

(51) Int. Cl.
*A61B 5/00* (2006.01)
*G06T 7/00* (2017.01)
*B82B 3/00* (2006.01)

(52) U.S. Cl.
CPC ............ *A61B 5/411* (2013.01); *A61B 5/6898* (2013.01); *B82B 3/0014* (2013.01); *G06T 7/0012* (2013.01)

(58) Field of Classification Search
None
See application file for complete search history.

(56) References Cited

U.S. PATENT DOCUMENTS

| | | | | |
|---|---|---|---|---|
| 3,496,703 A | * | 2/1970 | Maguire | A62B 18/006 96/296 |
| 6,466,133 B1 | | 10/2002 | Skardon | |
| 6,629,932 B2 | | 10/2003 | Weber et al. | |
| 6,992,580 B2 | * | 1/2006 | Kotzin | G08B 21/0453 340/539.11 |
| 7,420,663 B2 | * | 9/2008 | Wang | G01J 3/02 356/72 |
| 8,947,656 B2 | * | 2/2015 | Cunningham | G01J 3/44 356/300 |
| 9,000,933 B2 | | 4/2015 | Ray et al. | |
| 9,921,105 B2 | * | 3/2018 | Assefa | G01J 3/0272 |

(Continued)

OTHER PUBLICATIONS

H. Yin, "Separation and electrochemical detection platform for portable individual PM2.5 monitoring," 2017 IEEE International Symposium on Circuits and Systems (ISCAS), Baltimore, MD, 2017, pp. 1-4.

(Continued)

*Primary Examiner* — Chico A Foxx
(74) *Attorney, Agent, or Firm* — Patterson + Sheridan, LLP

(57) ABSTRACT

A wearable electronic device may alert a wearer as to a presence of either a range of allergens or to specific pollen to which the individual is allergic. As such, the device may warn the user of bioparticles likely to affect them allergenically. The device may include an airflow path. A deterministic lateral displacement (DLD) array may be positioned within the airflow path to capture bioparticles of a particular size. An imaging device may capture images of captured bioparticles. The system may include a database of bioparticles in a range of sizes. The system may be configured to compare the captured bioparticles to the information in the database. A wearer may be alerted if bioparticles potentially allergenically problematic to the person have been found in the captured bioparticles.

20 Claims, 8 Drawing Sheets

(56) References Cited

U.S. PATENT DOCUMENTS

| | | | |
|---|---|---|---|
| 2006/0206010 A1* | 9/2006 | Iida | A61B 5/0002 600/300 |
| 2009/0000188 A1* | 1/2009 | Sayers | A01G 7/00 47/58.1 R |
| 2012/0045826 A1* | 2/2012 | Yantz | G01N 21/253 435/288.7 |
| 2014/0102442 A1* | 4/2014 | Wilson | F24F 9/00 128/200.28 |
| 2014/0281479 A1* | 9/2014 | Gettings | G01N 33/0062 713/150 |
| 2016/0116181 A1 | 4/2016 | Aultman et al. | |
| 2016/0139012 A1* | 5/2016 | D'Silva | B01L 3/502753 424/93.7 |
| 2016/0146718 A1* | 5/2016 | Astier | G01N 15/1031 506/39 |
| 2016/0256097 A1* | 9/2016 | Manautou | A61B 5/411 |
| 2016/0290912 A1* | 10/2016 | Kent | G01N 15/1434 |
| 2016/0320306 A1* | 11/2016 | Huffman | G01N 21/85 |
| 2017/0095157 A1* | 4/2017 | Tzvieli | A61B 5/0077 |
| 2017/0108236 A1* | 4/2017 | Guan | G05B 15/02 |
| 2018/0070873 A1* | 3/2018 | Cronin | A61B 5/411 |
| 2018/0078939 A1* | 3/2018 | Hu | B01L 3/502761 |
| 2018/0231576 A1* | 8/2018 | Hu | B01L 9/527 |
| 2019/0245712 A1* | 8/2019 | Yu | H04L 12/4625 |
| 2019/0293539 A1* | 9/2019 | Manautou | G01N 33/4925 |

OTHER PUBLICATIONS

K. Hart, "TZOA Wearable Air Quality Tracker." <https://www.indiegogo.com/projects/tzoa-wearable-air-quality-tracker#/> [Accessed Mar. 11, 2018].

Aircasting, "AirBeam2," http://www.takingspace.org/aircasting/airbeam/ [Accessed Mar. 11, 2018].

H. Hojaiji, "Temperature and humidity calibration of a low-cost wireless dust sensor for real-time monitoring," 2017 IEEE Sensors Applications Symposium (SAS), Glassboro, NJ, 2017, pp. 1-6.

K. Hu, "Personalising pollution exposure estimates using wearable activity sensors," 2014 IEEE Ninth International Conference on Intelligent Sensors, Sensor Networks and Information Processing (ISSNIP), Singapore, 2014, pp. 1-6.

Zheng Zhang, Jiang Zhe, Santanu Chandra, Jun Hu, "An electronic pollen detection method using Coulter counting principle," Atmospheric Environment, vol. 39, Issue 30, Sep. 2005, pp. 5446-5453.

"Pollen Sensor", Pollen Sensor distinguish between pollen and dust | Shinyei Technology, 2016, http://www.shinyei.co.jp/stc/eng/optical/main_poln.html.

Shashi Ranjan,Kerwin Kwek Zeming, Roland Jureen, Dale Fisher, and Yong Zhang, "DLD pillar shape design for efficient separation of spherical and non-spherical bioparticles," Royal Society of Chemistry, Accepted Aug. 26, 2014.

Yulung Sung, Fernando Campa, and Wei-Chuan Shih, "Open-source do-it-yourself multi-color fluorescence smartphone microscopy," vol. 8, No. 11 | Nov. 1, 2017 | Biomedical Optics Express 5075.

J. McGrath, M. Jimenez and H. Bridle, "Deterministic lateral displacement for particle separation: a review," Lab Chip, 2014, 14, 4139.

Benjamin H. Wunsch, Joshua T. Smith, Stacey M. Gifford, ChaoWang, Markus Brink, Robert L. Bruce, Robert H. Austin, Gustavo Stolovitzky and Yann Astier, Nanoscale lateral displacement arrays for the separation of exosomes and colloids down to 20 nm, DOI: 10.1038/NNANO.2016.134.

* cited by examiner

US 10,820,852 B2

ALLERGIC EARLY DETECTION WEARABLE DEVICE

BACKGROUND

The present invention relates to medical devices, and more specifically, to devices used to detect respiratory aggravating particulates.

Respiratory irritants, such as pollen, pollution, and other plant and animal airborne particulates, are typical triggers leading to allergic attacks. To combat allergic episodes, an individual may elect to undergo a skin prick test to determine a source of an allergy. Once determined, the allergy sufferer may adopt one of several treatment options, such as antihistamines, prescription medications, or allergy shots. To mitigate attacks, an individual may take preemptive actions, such as taking medication before symptoms appear and closing windows. To this end, a proactive person may reference a regional weather report to check a pollen count, for instance. Although all of the above measures are commendable, it is desirable to know the pollen count in both a timely manner and in a specific location.

SUMMARY

According to one particular embodiment, an apparatus may include an airflow path and a displacement array positioned within the airflow path to capture the bioparticles of a particular size that are likely to affect a wearer. The apparatus further comprises an imaging device to capture images of the captured bioparticles; a database of information relating to a stored bioparticle, and an interface to communicate a condition to the wearer. A processor may be used to compare the captured bioparticles against the database and alert the wearer via the interface if bioparticles potentially allergenically problematic to the wearer have been found in the captured bioparticles.

According to another particular embodiment, a computer-implemented method of alerting a wearer of a device of an impending allergic attack may include capturing bioparticles of a particular size using a displacement array positioned within an airflow path of a wearable device. The method may include capturing images of the captured bioparticles; storing information relating to a stored bioparticle within a database; providing an interface to communicate a condition to a wearer of the wearable device, and comparing the captured bioparticles against the database and alerting the wearer via the interface if bioparticles potentially allergenically problematic to the wearer have been found in the captured bioparticles.

According to another particular embodiment, a program product is configured to alert a wearer of a device to a presence of an allergen, the program product comprising a computer readable storage medium having computer readable program code embodied therewith, the computer readable program code executable by a processor to access the memory and to execute the program code to initiate capturing images of bioparticles of a particular size channeled using a displacement array positioned within an airflow path within the wearable device, to store information relating to a stored bioparticle within a database; to provide an interface to communicate a condition to a wearer of the wearable device, and to compare the captured bioparticles against the database and alert the wearer via the interface if bioparticles potentially allergenically problematic to the wearer have been found in the captured bioparticles.

DETAILED DESCRIPTION

Figure 1:
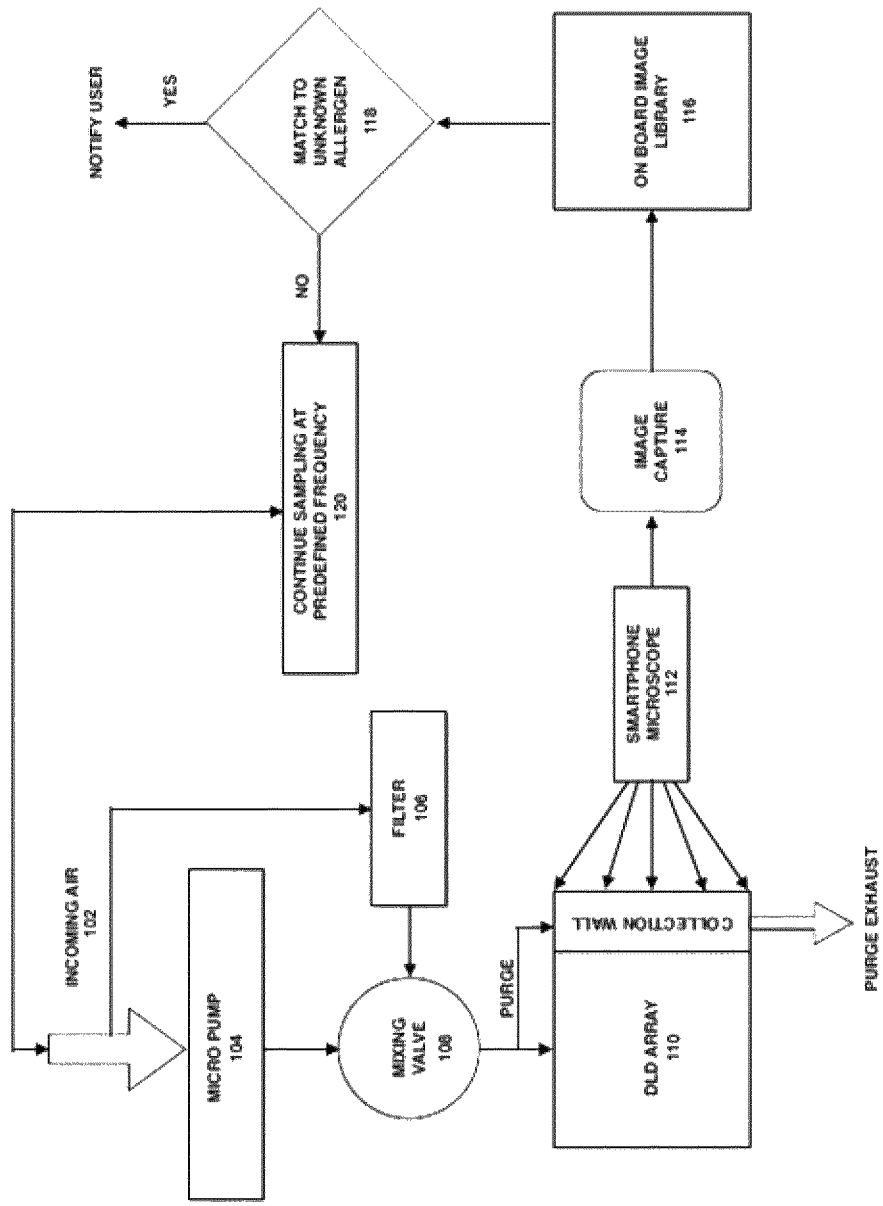
FIG. 1 is a block diagram of an embodiment of a system comprising a wearable device configured to detect airborne, particulate irritants that could initiate an allergic or asthmatic attack.

An embodiment includes a wearable electronic device that may alert a wearer as to a presence of either a range of allergens or to specific pollen to which the wearer is allergic. As such, the device may warn the user of bioparticles likely to affect them allergenically. To this end, the device may include an airflow path. A deterministic lateral displacement (DLD) array may be positioned within the airflow path to capture bioparticles of a particular size. An imaging device may capture images of captured bioparticles. The system may include a database of bioparticles in a range of sizes. The system may be configured to compare the captured bioparticles to the information in the database. A wearer may be alerted if bioparticles potentially allergenically problematic to the person have been found in the captured bioparticles.

An embodiment of the system uses both or at least one of deterministic lateral displacement (DLD) pillar arrays and nanoscale lateral displacement arrays for the separation of exosomes and colloids. The DLD pillar arrays may facilitate an efficient separation of spherical and non-spherical bioparticles. For example, illustrative DLD separation may achieve particle separation down to 20 nm. The system may use a microscope (e.g., 400×) incorporated into a smartphone. Smartphone microscopy of an embodiment may enable the identification of features of about 2 um and smaller.

The wearable device of an embodiment may include a flat camera that images a fluidized stream of ambient air. As discussed herein, the camera may have microscopic capabilities. The ambient air may be sorted via a suitably sized nano-DLD. For example, the pillars of the DLD array may be spaced according to the most common pollen sizes (e.g., 6-100 um).

An image capture may be set at a predetermined rate (e.g., once per minute or every ten minutes) for each of the capture wells in the DLD array. The captured images may be compared to the onboard database images. The device manufacturer may construct a database of allergen identifying data (e.g., photographs) of common allergens (e.g., ragweed, ryegrass, etc.). If a match occurs, the user may be notified and prompted to take appropriate action. For example, a display may remind a user to take medicine or to close their windows. Over time, the device may learn (e.g., machine learning processes) which allergen triggers a response. The user may thus be enabled to program the wearable device to only alert them when a specific allergen is detected.

Through the selection of the pillar geometry and spacing (e.g., a pillar pitch, row-to-row shift, etc.), the system may efficiently sort both spherical and non-spherical particles in the size regime of the most common pollen allergens. As described herein, bumping and other displacement modes may sort the particles along the length of the DLD array to a collection wall. Consequently, imaging the collection wall at predefined intervals enables a photo record of the sorted allergens based on size. The sampling frequency may be adjusted to suit the individual. In those cases where the pollen count may be high, the incoming air may be diluted with a filtered air source to minimize particle-particle interactions that would interfere with the lateral displacement of discrete particles.

Turning now to the Drawings, FIG. 1 is a block diagram of an embodiment of a system 100 and associated processes comprising a wearable device configured to detect airborne, particulate irritants that could initiate an allergic or asthmatic attack. In this manner, the device may warn the user of bioparticles likely to affect them allergenically.

As represented in FIG. 1, the system 100 may receive an airflow 102. Where desired, the airflow may be facilitated by a pump 104. Where dilution is advantageous, the system 100 may use a filter 106 and mixing valve 108 to dilute the primary airflow 102. In those cases where the pollen count may be high, the incoming air 102 may be diluted with the filtered/mixed air to minimize particle-particle interactions that would interfere with the lateral displacement of discrete particles.

A DLD array 110 may be positioned within the airflow path to capture bioparticles of a particular size. DLD is a technology that utilizes the specific arrangement of posts (e.g., protrusions/extensions) within a channel to precisely control the trajectory of and facilitate separation of particles larger and smaller than a critical diameter.

As explained herein, each succeeding row within a constriction is shifted laterally at a set distance from the predecessor, this leads to the creation of separate flow laminar which follow known paths through the device. The separation mechanism of DLD works in that if the center of a particle is out with the width of the first streamline, it then becomes displaced into the second streamline when negotiating a post. This action continues each time such a particle passes a post, with the particle said to be larger than the critical diameter. Meanwhile, particles that are smaller than critical diameter remain centered within the first streamline and follow the defined route of this streamline through the device. Particles smaller and larger than the critical diameter will then be separated from one another along the length of a device.

An imaging device, such as a smartphone microscope 112 coupled to an image capture device 114 may capture images of the bioparticles. An illustrative microscopic imaging platform may include a bright-field, oblique-angle fluorescence, epi-fluorescence, or phase-contrast microscopic imaging.

The system 100 may include a database, or library 116, of bioparticles in a range of sizes. The system 100 may be configured to compare the captured bioparticles to the information in the library 116. A wearer may be alerted at 118 if bioparticles potentially allergenically problematic to the person have been found in the captured bioparticles. Sampling may continue at 120 at determined frequency. Although the foregoing diagram illustrates the DLD array coupled to a smartphone microscope, other embodiments envision the microscope coupled directly to the DLD array. Additionally, the incoming air of another embodiment may go through the pump. The mixing valve may determine the ratio of direct air to filter air if required so the air out of pump may go into the mixing valve and may be split and proportioned to either go directly to the DLD, through the filter, and then to DLD array or as a ratio of each going into the filter based on whether dilution is advantageous.

Figure 2:
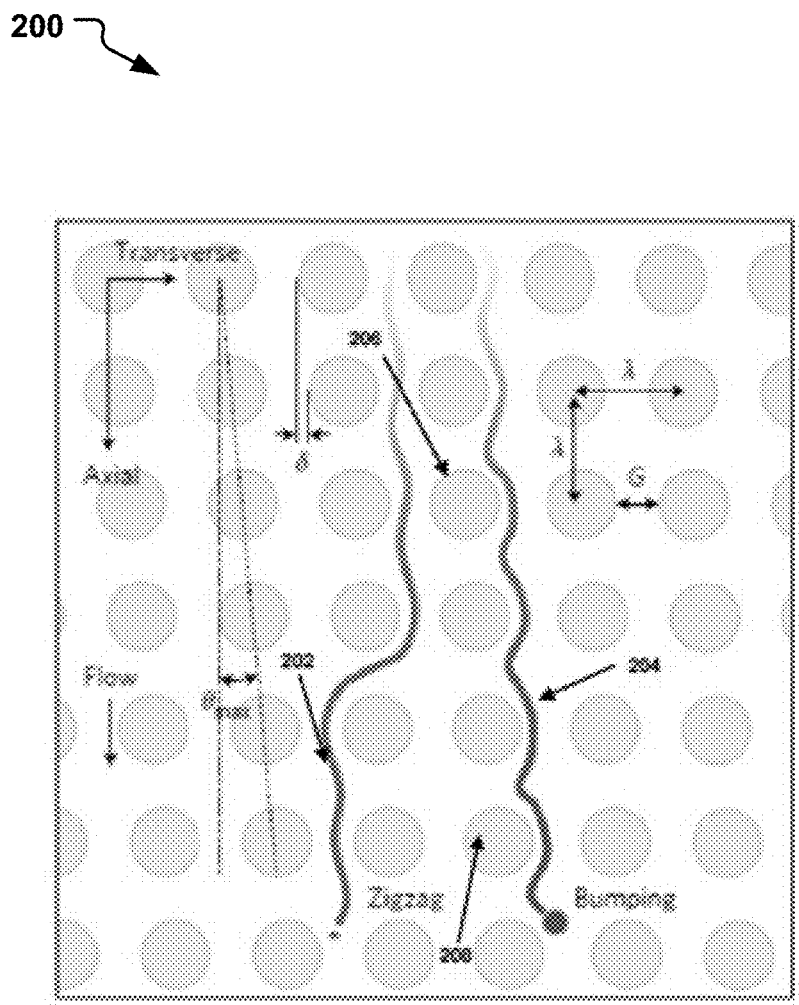
FIG. 2 is a cross-sectional view of an array configured to sort and capture airborne particulates for examination, detection, identification, risk assessment, and other analysis. The DLD array may be similar to the array of FIG. 1.

FIG. 2 is a schematic representation of a pillar array 200 that illustrates the array parameters of maximum angle, $\theta$max, pillar gap size, G, pillar pitch, $\lambda$, and row-to-row shift, $\delta$. Trajectories for particles with diameter below the nominal critical diameter follow a laminar flow in a zigzag mode 202, whereas larger particles with a diameter larger then the critical diameter follow $\theta$max in a bumping mode 204 (e.g., bumping on pillars 206, 208).

Using combinations of protrusions and grooves, three-dimensional spherical particles, two-dimensional, and different shaped particles may be separated by the system 200. The arrangement of pillar protrusions and grooves induces inertial movements, enhancing the separation of spherical particles. Secondly, non-spherical particles experience dominant rotational movements due to the protrusions and grooves which help in changing their orientations.

Figure 3:
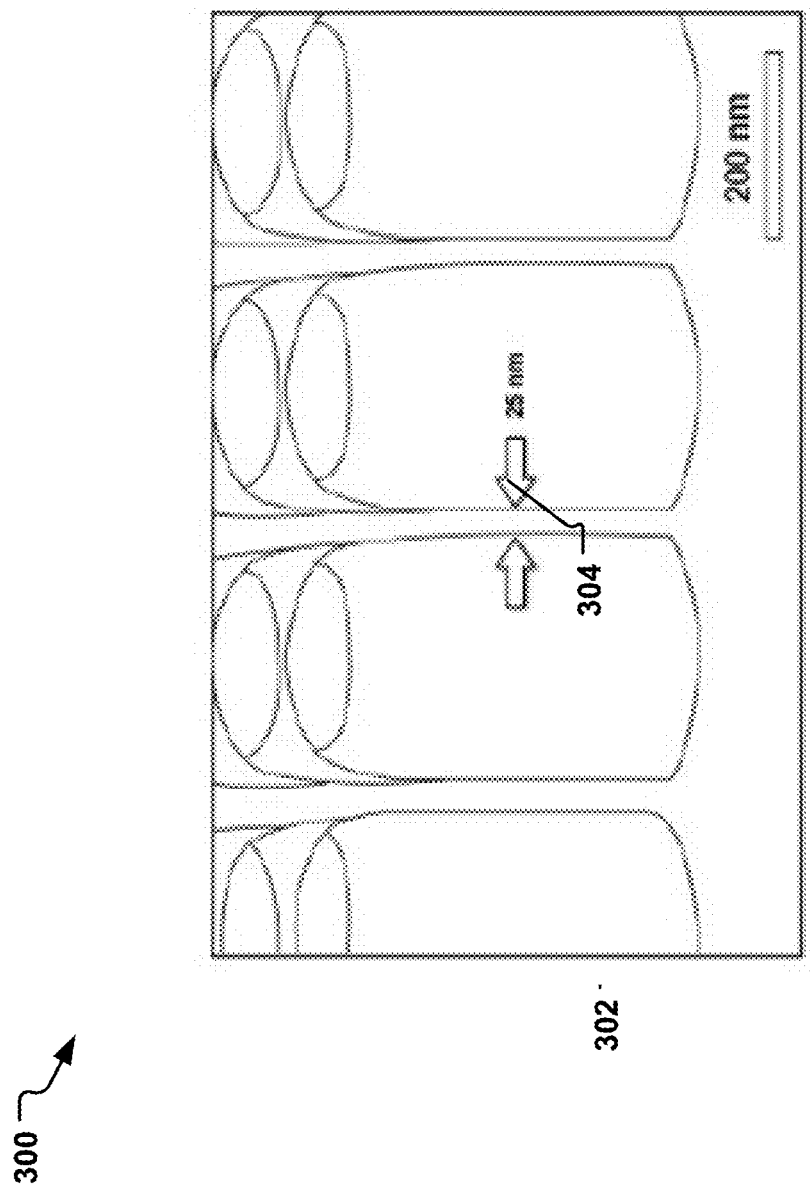
FIG. 3 is a schematic representation of the array concept as may be employed in the array of FIG. 2.

FIG. 3 is a magnified, perspective view of a DLD array 300 as may be employed in the DLD array of FIG. 2. The rendering is such that might be taken with an electron microscope to show details of a configuration of pillars 302. As shown, the pillars in the illustrative arrangement are spaced 25 nm from one another. Based on tolerance and other factors, the pillars themselves might have slightly different spacing than the allergens they filter.

The DLD array 300 includes a pillar gradient array that has a specific critical size for particle separation with respective pillar spacing and array gradient. Particles larger than the critical size are bumped off their flow path and displaced laterally from their original fluid stream to follow the pillar gradient, while smaller particles will continue the path unaffected by the DLD pillar array 300.

One skilled in the art will appreciate that while pillar shapes, such as shown in FIG. 3, significantly affect bioparticle separation, other shapes with protrusions and groove structures may alternatively be used to induce particle rotation while pillar grooves may confine the particle rotational movement in a directed path for effective separation in a DLD pillar array.

Figure 4:
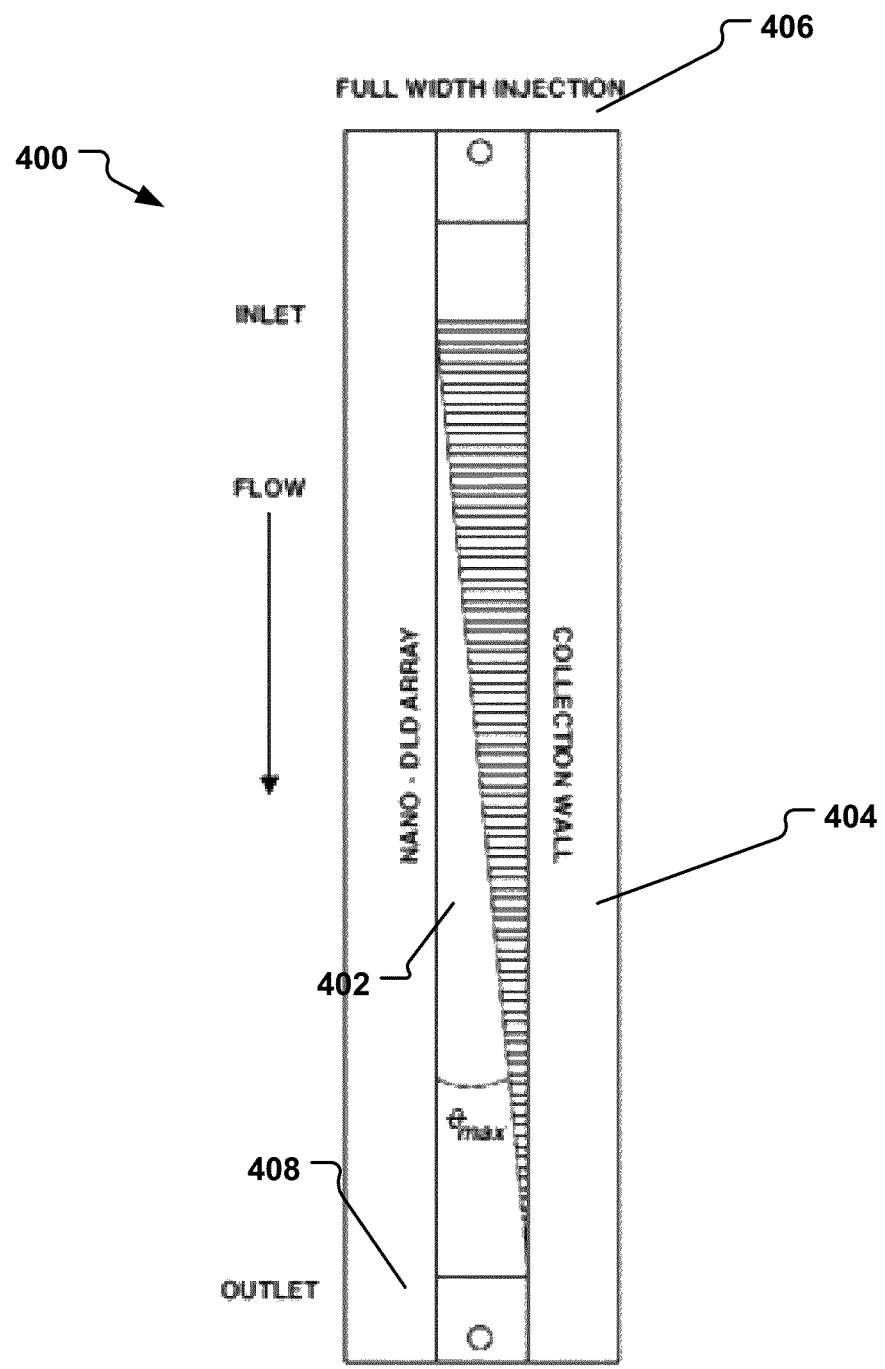
FIG. 4 is a cross-sectional view of a DLD array as may be included in the system 100 of FIG. 1.

FIG. 4 is a cross-sectional view of a DLD array device 400 configured to sort and capture airborne particulates for examination, detection, identification, risk assessment, and other analysis. The DLD array device 400 may be similar to the DLD array 110 of FIG. 1. As shown in FIG. 4, the DLD array device 400 may include in a DLD region 402 and a capture wall 404 to receive sorted particles. As described herein, bioparticles flowing in through an inlet 406 and out an outlet 408 are sorted and imaged (e.g., at the capture wall 404).

Figure 5:
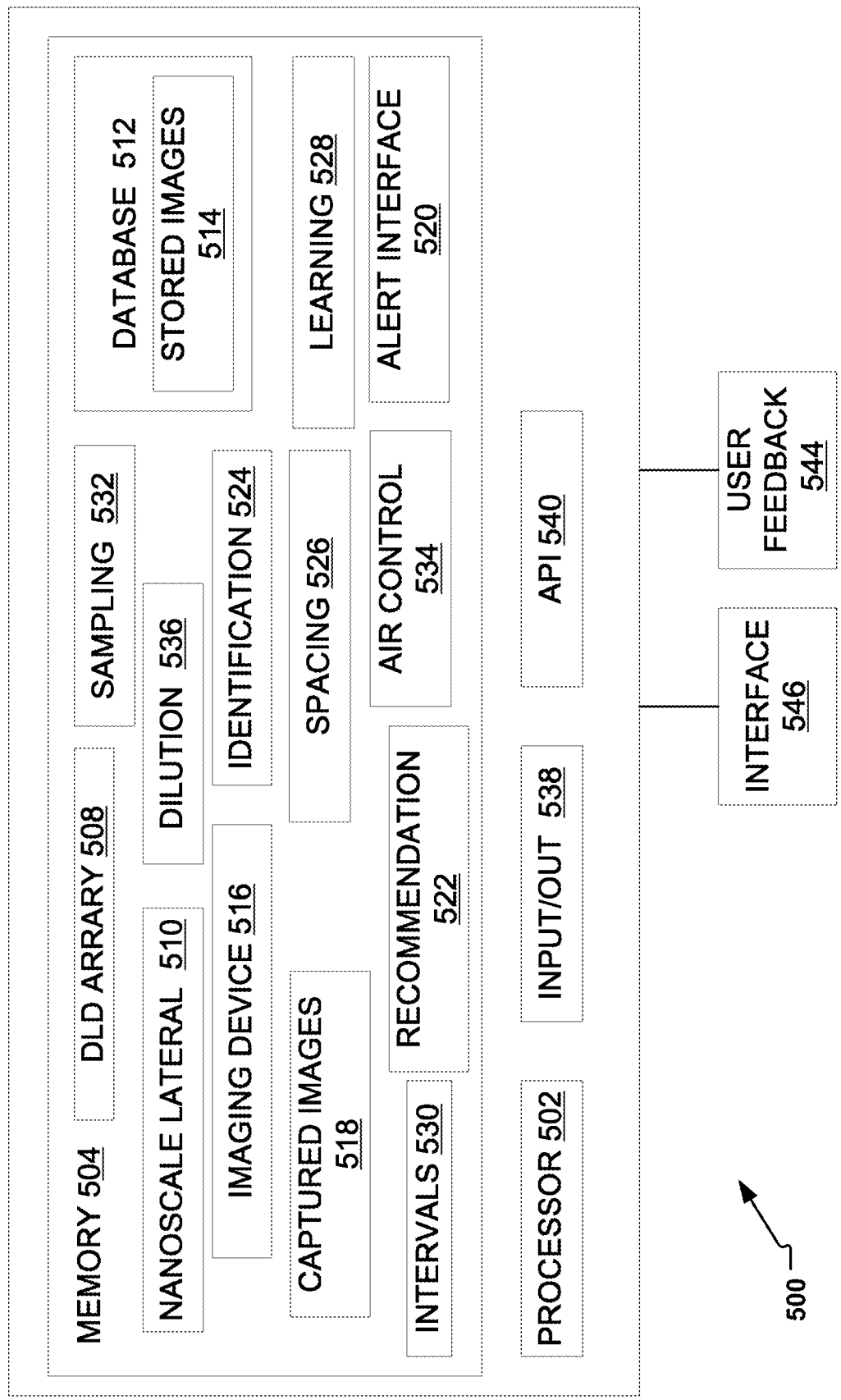
FIG. 5 is a block diagram of an embodiment of a system configured to detect, analyze, assess, and report an imminent threat of airborne particulate irritants.

FIG. 5 is a block diagram of an embodiment of a system 500 configured to detect, analyze, assess, and report an imminent threat of airborne particulate irritants. The illustrative system 500 includes a processor 502 and a memory 504. As represented in the block diagram, the memory 504 includes a DLD array 508, a nanoscale lateral array 510, and a database 512. The database 512 may store bioparticle images 514 of different types of bioparticles.

The system 500 may include an imaging device module 516, as well as captured images 518 photographed by the imaging device module 516. An alert interface module 520 may output preemptory advice from a recommended action module 522. The memory 504 may also include an identification module 524, a spacing determination module 526, a learning module 528, and an interval determination module 530. As shown in FIG. 5, the system also includes a sampling frequency module 532, a filtered air control module 534, and a dilution determination module 536.

The system 500 may additionally include an input/output (I/O) 538 module and an application program interface (API) 540 to receive user requests 542 and user feedback 544. To facilitate this interaction, the system may include a user interface 546.

Figure 6:
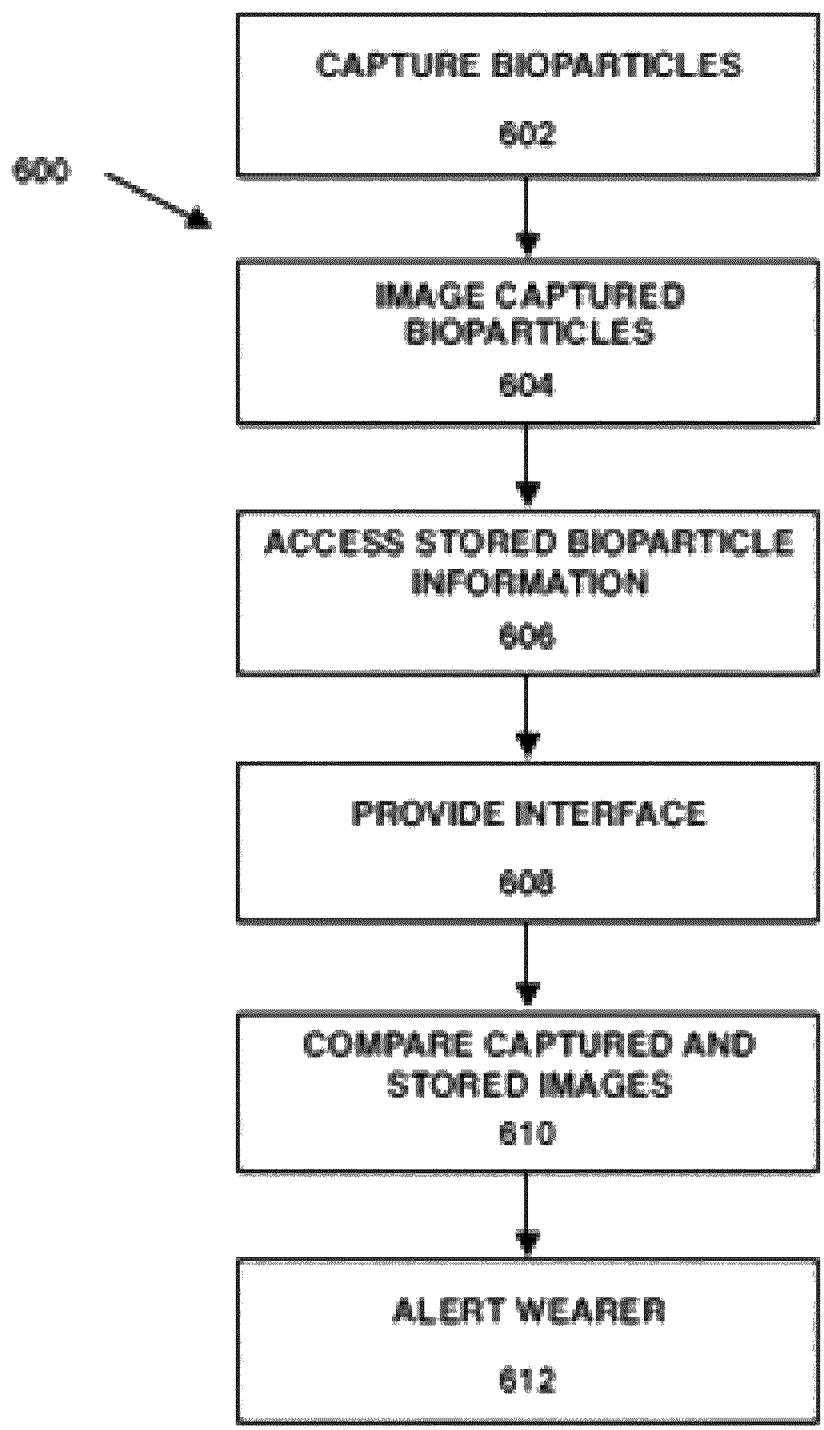
FIG. 6 is a flowchart of an embodiment of method of allowing a wearer of a device to be informed regarding a type and an amount of potential airborne irritants.

FIG. 6 is a flowchart of an embodiment of a computer-implemented method 600 of allowing a wearer of a device to be informed regarding a type and an amount of potential airborne irritants, as well as of an impending allergic attack. The method 600 may include capturing bioparticles of a particular size at 602. The particles may be captured using a displacement array positioned within an airflow path of a wearable device. The size of the captured particles may correspond to allergens known to affect a wearer.

At 604, the method 600 may use magnification and a camera to image the captured bioparticles. For instance, a smartphone may include a microscopic imaging platform. For example, a platform may include a bright-field, oblique-angle fluorescence, epi-fluorescence, or phase-contrast microscopic imaging for bioparticle identification.

At 606, the method 600 may store and access information relating to a stored bioparticle within a database. The stored bioparticle may be one of a plurality of catalogued and learned allergens.

The method 600 may provide at 608 an interface to communicate a condition to a wearer of the wearable device. At 610, the method 600 may compare the captured bioparticles against the database. The wearer may be alerted at 612 via the interface if bioparticles potentially allergenically problematic to the wearer have been found in the captured bioparticles.

Figure 7:
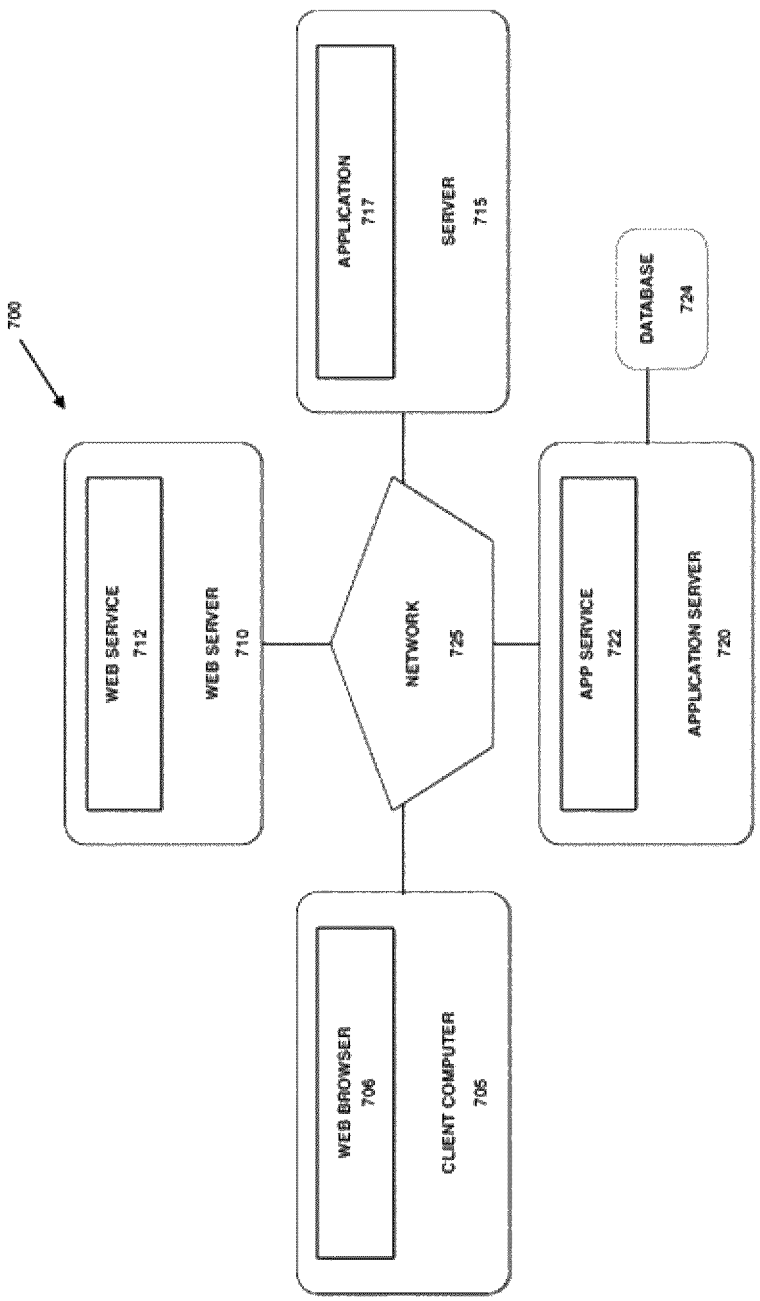
FIG. 7 illustrates another example computing system according to one embodiment, such as may be realized using a networked environment to notify a wearer of an impending allergic attack.

FIG. 7 illustrates another example computing system according to one embodiment, such as may be realized using a networked environment. As shown, the computing environment 700 includes a client computer 705, a web server 710, a server 715, and an application server 720. The client computer 705 may be a physical system (e.g., a desktop, laptop computer, mobile device, etc.) or a virtual computing instance executing in the cloud. The client computer 705 includes a web browser 706. A user may access data services through the web browser 707 over a network 725 (e.g., the Internet).

For instance, a user may access a web service 712 executing on a web server 710. In one embodiment, the web service 712 provides a web interface for an application server 720 (e.g., executing an application service 722). More specifically, the application service 722 provides a database 724. The database 724 may include data presented to users on the web browser 707.

Figure 8:
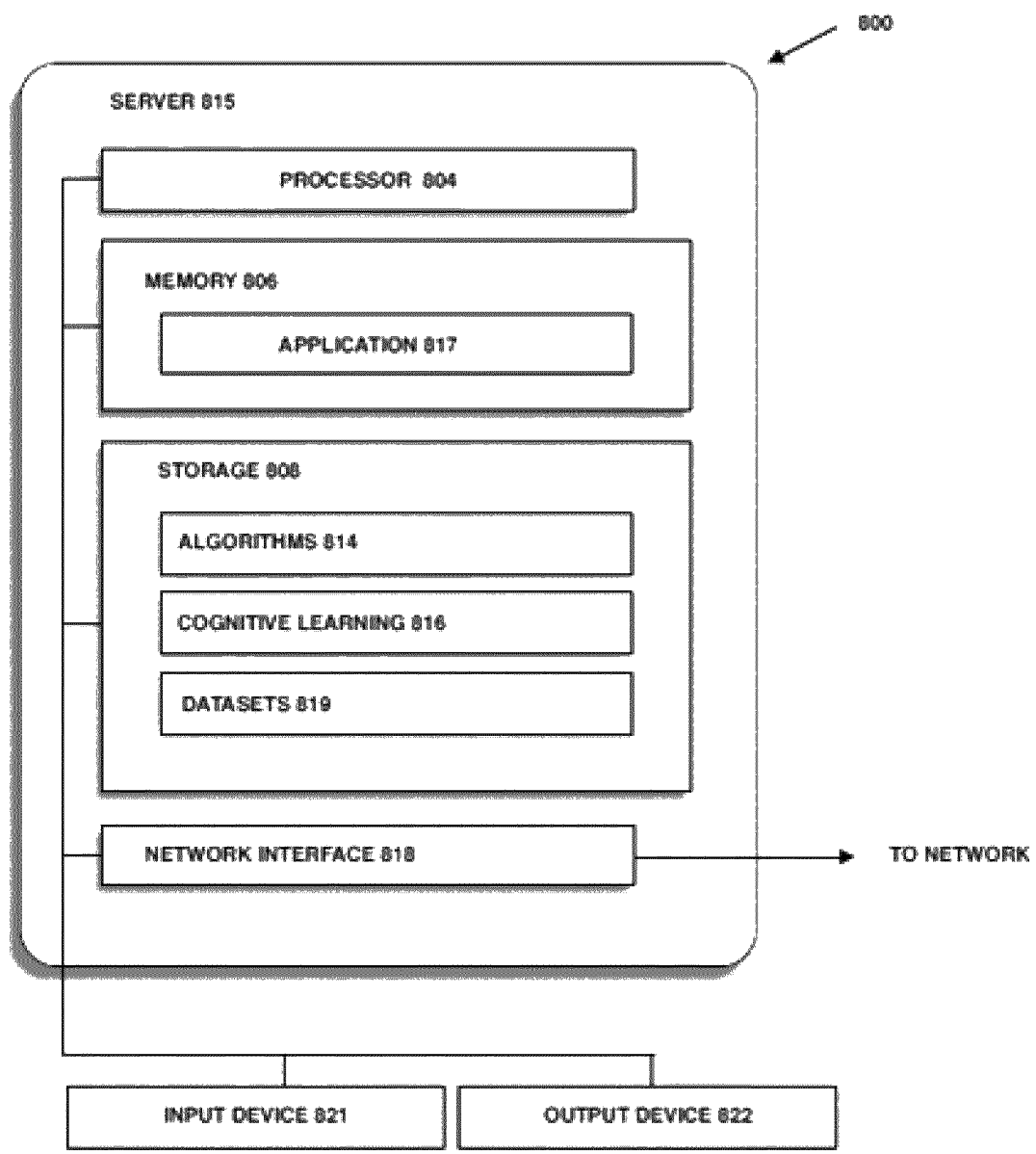
FIG. 8 further illustrates a server, such as the server of FIG. 7, according to one embodiment.

FIG. 8 further illustrates a server 815, such as the server 715 of FIG. 7, according to one embodiment. The server 815 generally includes a processor 804 connected via a bus to a memory 806, a network interface device 818, a storage 808, an input device 821, and an output device 824. The server 815 is generally under the control of an operating system. Examples of operating systems include the UNIX operating system, versions of the Microsoft Windows operating system, and distributions of the Linux operating system (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both). More generally, any operating system supporting the functions disclosed herein may be used. The processor 804 is included to be representative of a single CPU, multiple CPUs, a single CPU having multiple processing cores, and the like. Similarly, the memory 806 may be a random access memory. While the memory 806 is shown as a single identity, it should be understood that the memory 806 may comprise a plurality of modules, and that the memory 806 may exist at multiple levels, from high speed registers and caches to lower speed but larger DRAM chips. The network interface device 818 may be any type of network communications device allowing the navigation server 810 to communicate with other computers via the network 825.

The storage 808 may be a persistent storage device. Although the storage 808 is shown as a single unit, the storage 808 may be a combination of fixed and/or removable storage devices, such as fixed disc drives, solid state drives, removable memory cards, optical storage and network storage systems.

As shown, the memory 806 contains the application 817, which may be an application generally executed to take actions described herein. Storage 808 contains the algorithms 814, cognitive learning 816, and datasets 819.

The input device 821 may provide a keyboard and/or a mouse, etc. The output device 822 may be any conventional display screen. Although shown separately from the input device 821, the output device 822 and input device 821 may be combined. For example, a display screen with an integrated touch-screen may be used.

The descriptions of the various embodiments of the present invention have been presented for purposes of illustration, but are not intended to be exhaustive or limited to the embodiments disclosed. Many modifications and variations may be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It may be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It may also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., threshold adjustment algorithms) or related data available in the cloud. For example, the modules of FIG. 1 could execute on a computing system in the cloud. In such a case, the threshold adjustment algorithms could adjust response thresholds and store the new values at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof. While certain embodiments are applicable to spoken language systems, the claims are not limited or even particularly applicable to spoken language interfaces. In one example, an embodiment of a method may not relate to speech modality. The scope thereof is thus determined by the claims that follow.

What is claimed is:

1. An apparatus comprising:
an airflow path;
a displacement array positioned within the airflow path to capture bioparticles of a particular size that are likely to affect a wearer;
an imaging device to capture images of the captured bioparticles, wherein the images are captured by the imaging device at a predetermined rate, and wherein the image capture is set at the predetermined rate for each of a plurality of capture wells of the displacement array;
a database of information relating to a stored bioparticle;
an interface to communicate a condition to the wearer; and
a processor to compare the captured bioparticles against the database and alert the wearer via the interface if bioparticles potentially allergenically problematic to the wearer have been found in the captured bioparticles.

2. The apparatus of claim 1, wherein the displacement array comprises a deterministic lateral displacement (DLD) array.

3. The apparatus of claim 1, wherein the displacement array comprises a nanoscale lateral displacement array.

4. The apparatus of claim 1, wherein the particular size is determined based on an allergy determined to affect the wearer.

5. The apparatus of claim 1, wherein the information relates to a plurality of stored bioparticles comprising a range of sizes.

6. The apparatus of claim 1, wherein the imaging device is configure to distinguish features as small as 2 μm.

7. The apparatus of claim 1, wherein a spacing of pillars of the displacement array are spaced around 6 μm to about 100 μm.

8. The apparatus of claim 1, wherein the processor is configured to select and initiate communicating an appropriate action to the wearer.

9. The apparatus of claim 1, wherein the processor is configured to learn which allergen triggers a response over time.

10. The apparatus of claim 1, wherein the wearer is alerted only when a specific allergen is detected.

11. The apparatus of claim 1, wherein the imaging device is configured to image a collection wall at predefined intervals.

12. The apparatus of claim 1, wherein the processor is configured to adjust a sampling frequency of the imaging device based on an attribute of the wearer.

13. The apparatus of claim 1, wherein the processor is configured to cause incoming air within the airflow path to be diluted with an air source.

14. The apparatus of claim 1, further comprising an air mixing valve in communication with the airflow path to dilute airflow through the airflow path.

15. A computer-implemented method of alerting a wearer of a device of an impending allergic attack, the method comprising:
capturing bioparticles of a particular size using a displacement array positioned within an airflow path of a wearable device;
diluting airflow through the airflow path using an air mixing valve;
capturing images of the captured bioparticles;
storing information relating to a stored bioparticle within a database;
providing an interface to communicate a condition to a wearer of the wearable device; and
comparing the captured bioparticles against the database and alerting the wearer via the interface if bioparticles potentially allergenically problematic to the wearer have been found in the captured bioparticles.

16. The method of claim 15, further comprising adjusting a sampling frequency of the imaging device based on an attribute of the wearer.

17. The method of claim 15, wherein the displacement array comprises a deterministic lateral displacement (DLD) array.

18. A non-transitive program product alerting a wearer of a device to a presence of an allergen, the program product comprising a computer readable storage medium having computer readable program code embodied therewith, the computer readable program code executable by a processor to access the memory and to execute the program code to:

initiate capturing images of bioparticles of a particular size channeled using a displacement array positioned within an airflow path within the wearable device, wherein the images are captured by the imaging device at a predetermined rate, and wherein the image capture is set at the predetermined rate for each of a plurality of capture wells of the displacement array;

store information relating to a stored bioparticle within a database;

provide an interface to communicate a condition to a wearer of the wearable device; and compare the captured bioparticles against the database and alert the wearer via the interface if bioparticles potentially allergenically problematic to the wearer have been found in the captured bioparticles.

19. The program product of claim 18, wherein the program code executable by the processor to initiate adjusting a sampling frequency of the imaging device based on an attribute of the wearer.

20. The program product of claim 18, wherein the program code executable by the processor to initiate learning which allergen triggers a response over time.

* * * * *